(12) United States Patent
Drauz et al.

(10) Patent No.: US 6,830,692 B1
(45) Date of Patent: *Dec. 14, 2004

(54) AMINO ACID COMPOSITION FOR HEMODIALYSIS

(75) Inventors: Karlheinz Drauz, Freigericht (DE); Guenter Knaup, Bruchkoebel (DE); Gerard Richet, Saint-Quentin (FR); Werner Kleophas, Duesseldorf (DE); Adolf Gruenert, Ulm (DE)

(73) Assignee: Degussa AG, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,743

(22) Filed: Sep. 20, 1999

(51) Int. Cl.$^7$ ...................... B01D 61/24; A61K 31/195
(52) U.S. Cl. ...................... 210/646; 210/647; 514/400; 514/419; 514/423; 514/556; 514/557; 514/561; 514/562; 514/564; 514/565; 514/567
(58) Field of Search ............................... 210/646, 647; 514/400, 419, 423, 556, 557, 561, 562, 564, 565, 567

(56) References Cited

U.S. PATENT DOCUMENTS 5,670,176 A * 9/1997 Martis et al. ............... 424/663

FOREIGN PATENT DOCUMENTS

DE  22 59 787  7/1973
DE  31 15 665  11/1982

OTHER PUBLICATIONS

Wilfred Druml, *Protein Metabolism in Acute Renal Failure, Mineral and Electrolyte Metabolism*, 1998: 24, pp. 47–54.
Carolyn L. Abitbol, M.D., et al., *Effects of Amino Acid Additives During Hemodialysis of Children, Journal of Parenteral and Enteral Nutrition*, vol. 8, No. 1, (1984), pp. 25–29.

T. Tepper, et al., *Amino Acids and Hemodialysis, Int. J. Artificial Org.*, 4, 208–10 (1981).

S. Troupel et al., *Plasma Free Amino Profiles and Nutrition Proteins in Chronic Renal Failure: Effect of Dialysis Treatment, Amino Acids*, vol. 2, (1992), pp. 127–132.

S. Fruend, et al., *The Addition of Aminoacids and Phosphate to Hemodiafiltration Solutions in Newborns with Hyperammonemic Coma, Clinical Nephrology*, vol. 46, (1996), pp. 64–66.

Joel D. Kopple, M.D., *Therapeutic Approaches to Malnutrition in Chronic Dialysis Patients: The Different Modalities of Nutritional Support, American Journal of Kidney Diseases*, vol. 33, No. 1 (1999), pp. 180–185.

Charles Chazot et al., *Dialytic Nutrition: Provision of Amino Acids in Dialysate During Hemodialysis, Kidney Intl.*, vol. 52, (1997), pp. 1663–1670.

*Kirk–Othmer Encyclopedia of Chemical Technology*, Fourth Edition, vol. 8, pp. 64–74.

F. Quarto di Palo, et al., *Clinical Use of a Dialysis Solution Containing Amino Acids, The International Journal of Artificial Organs*, vol. 1., No. 1, (1978) pp. 112–113.

* cited by examiner

Primary Examiner—John Kim
(74) Attorney, Agent, or Firm—Oblon, Spivak, McClelland, Maier & Neustadt, P.C.

(57) ABSTRACT

The invention relates to a special amino acid mixture for hemodialysis as well as to the dialysis solution that can be prepared from the amino acid mixture. When the amino acid mixtures according to the invention are used for such purposes, the "shrinking men" phenomenon cam be prevented. The present invention also relates to a hemodialysis process and apparatus. This aspect of the invention provides a closed dialysis system with a dialyzer solution containing the amino acid mixtures according to the invention.

9 Claims, 3 Drawing Sheets

AMINO ACID COMPOSITION FOR HEMODIALYSIS

BACKGROUND OF THE INVENTION

1. Field of the Invention

The present invention relates to a special amino acid mixture and dialysis solution for hemodialysis. The use of the amino acid mixture for preparing a solution suitable for hemodialysis is also set forth. The present invention also relates to a method and an apparatus for hemodialysis.

2. Discussion of the Background

Patients who suffer from impaired kidney function, or who do not even have kidneys, need the assistance of an external blood-purification system to purify the blood of toxic metabolic products. In such cases, peritoneal dialysis and hemodialysis have proved to be the methods of choice.

Heretofore, however, neither form of dialysis has completely made up for the lack of kidney function. In the case of hemodialysis, for example, a phenomenon known commonly as "shrinking man" becomes evident after prolonged treatment. This syndrome is blamed substantially on a protein-deficient nutritional condition. This deficiency condition has several causes, such as protein and energy metabolism disorders, hormonal imbalance and poor nutrient intake, and in the case of dialysis patients is greatly exacerbated by the net loss of amino acids from the plasma during dialysis, thus depriving the body of its needs for normal functioning.

Various therapies are currently being used to prevent and treat this deficiency condition (J. D. Kopple, Am. J. Kidney Diseases, 33, 180–185 (1999)). Besides special diets and nutrient supplements, dialysis patients sometimes also receive additional nutrients by artificial means. Besides enteral nutrition by esophageal tube, parenteral nutrition is also used. In this situation, the amino acids in the form of concentrated solution are either administered directly by means of a central venous catheter or are added to the blood returned to the body during dialysis treatment.

Although amino acid solutions of specially adapted composition (W. Druml, Miner. Electrolyte Metab., 24, 47–54 (1998)) have been used in certain cases for such parenteral nutrition, a satisfactory nutritional condition cannot be achieved with any of these methods (J. D. Kopple, Am. J. Kidney Diseases, 33, 180–185 (1999)). The reason is that, although the general nutritional condition is indeed improved by the additional nutrient supply, the disturbed protein metabolism which results from loss of kidney activity and which in turn leads among other consequences to unbalanced amino acid composition (S. Troupel et al., Amino Acids 2, 127–132 (1992)) is not alleviated, but instead can even be further exacerbated, since the supplied infusion solutions are oriented to the physiological condition and have a composition adjusted such that their relative concentrations of amino acids corresponds to the uptake thereof from the plasma into the cells and thus not to the concentration pattern of the plasma itself. Furthermore, when the amino acid solution is supplied during dialysis, a large part of the supplied amino acids is immediately removed once again via the dialyzer fluid.

Some attempts have therefore been made, by adding amino acids to the dialyzer solution in the concentration which exists in the plasma, to prevent at least the additional amino acid losses which occur during dialysis. All solutions used heretofore, however, lack the complete physiological spectrum of amino acids necessary (F. Quarto di Paolo et al., Int. J. Art. org., 1978, 1, pp. 112 ff.; C. L. Abitol et al., J. Parenteral and Enteral Nutrition, 1984, 8, pp. 25 ff.; S. FriAnd et al., Clinical Nephrology, 46, 64–66 (1996); C. Chazot et al., Kidney Int. 52, 1663–1670 (1997)). In fact, the already existing imbalances are even exacerbated by such measures. This dialysis method has therefore not been adopted as routine therapy, and has even been evaluated as too expensive and ineffective (T. Tepper et al., Int. J. Artificial Org. 4, 208–10 (1981)).

Accordingly, there remains a need for compositions suitable for hemodialysis which overcome the difficulties described above, and to methods of dialysis using such compositions.

SUMMARY OF THE INVENTION

It is an object of the present invention to provide an amino acid composition which is capable of preventing the loss of amino acids from the plasma of a patient undergoing hemodialysis.

It is another object of the present invention to provide an amino acid composition which can be used to compensate for pathological amino acid imbalances in the plasma of a patient undergoing hemodialysis.

It is an another object of the present invention to provide an amino acid composition which, as compared to known compositions, is capable, to a higher degree, of preventing the loss of amino acids from the plasma of a patient undergoing hemodialysis and which can be used to compensate for pathological amino acid imbalances in the plasma of a patient undergoing hemodialysis.

The objects of the invention, and others, may be accomplished with an amino acid composition comprising the following proportion of amino acids, based on the total weight of the amino acids:

TABLE 1

|     | wt % Lower Limit | wt % Upper Limit |
| --- | --- | --- |
| Gln | 15.2 | 22.8 |
| Ala | 7.6 | 11.4 |
| Pro | 6.0 | 9.0 |
| Val | 6.0 | 9.0 |
| Gly | 3.7 | 5.5 |
| Lys | 6.6 | 9.8 |
| Leu | 3.7 | 5.5 |
| Thr | 3.1 | 4.7 |
| Ser | 2.4 | 3.5 |
| Arg | 4.2 | 6.3 |
| His | 2.9 | 4.3 |
| Ile | 1.8 | 2.8 |
| Tyr | 2.4 | 3.5 |
| Orn | 2.4 | 3.5 |
| Glu | 1.8 | 2.8 |
| Phe | 2.1 | 3.1 |
| Cys | 2.9 | 4.3 |
| Asn | 1.3 | 2.0 |
| Trp | 1.6 | 2.4 |
| Cit | 1.0 | 1.6 |
| Met | 0.8 | 1.2 |
| Abu | 0.0 | 0.5 |
| Asp | 0.5 | 0.8 |

The results of using this amino acid composition containing all relevant amino acids for hemodialysis are, on the one hand, that the amino acid concentration imbalances in the blood plasma of sick patients are compensated for and, on the other hand, that amino acid migration into the dialyzate due to lack of osmotic pressure is prevented.

Thus, the objects of the present invention may also be accomplished with a dialyzer fluid containing the proportions of the amino acids described above.

The objects of the present invention may also be accomplished with dialyzer fluid comprising amino acids at the following concentrations:

| Amino Acid | Concentration (μmol/l) | Amino Acid | Concentration (μmol/l) | Amino Acid | Concentration (μmol/l) |
|---|---|---|---|---|---|
| Gln | 401.8–663.9 | Thr | 103.2–169.1 | Glu | 39.5–88.9 |
| Ala | 339.7–555.2 | Ser | 84.9–138.5 | Phe | 49.1–79.0 |
| Pro | 178.1–355.5 | Arg | 70.1–130.9 | Cys | 50.9–70.0 |
| Val | 206.9–320.8 | His | 76.9–111.8 | Asn | 23.5–61.4 |
| Gly | 175.8–303.9 | Ile | 50.1–99.9 | Trp | 18.4–58.2 |
| Lys | 136.0–231.9 | Tyr | 50.4–91.4 | Cit | 19.3–42.1 |
| Leu | 95.8–180.1 | Orn | 52.2–85.8 | Met | 16.6–33.4 |
| Abu | 10.4–31.8 | Asp | 13.0–22.1 | | |

The objects of the present invention may also be accomplished with a method of hemodialysis by dialyzing a patient in need thereof using the inventive amino acid composition.

The objects of the present invention may also be accomplished with a method of hemodialysis by dialyzing a patient in need thereof with a dialyzer fluid containing the amino acid composition of the invention.

The objects of the present invention may also be accomplished with an apparatus for hemodialysis with a dialyzer, comprising:

a first flow path for the blood of a patient, a second flow path for a dialyzer fluid, a semipermeable membrane separating the first and second flow paths, a vessel for containing the dialyzer fluid, wherein the vessel has a connection for withdrawal of dialyzer fluid to be supplied by the dialyzer and has a connection for the return to the vessel of the dialyzer fluid arriving from the dialyzer, wherein the vessel is sufficiently thermally insulated from the ambient air that there is no need for a heating means to control the temperature of the dialyzer fluid and to keep it constant throughout the duration of the dialysis treatment, wherein the connection for withdrawal of the dialyzer fluid discharges at the upper region of the vessel and the connection for return of the dialyzer fluid discharges in the lower region of the vessel, wherein the vessel contains a dialyzer fluid containing the amino acid composition of the present invention.

The amino acid composition according to the invention may be added to a dialyzer solution in the proportion required to obtain a dialyzer fluid which corresponds in composition and concentration to the amino acid plasma level of a healthy person. The subject matter of the invention, therefore, also includes a dialysis solution having the amino acid composition described above.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
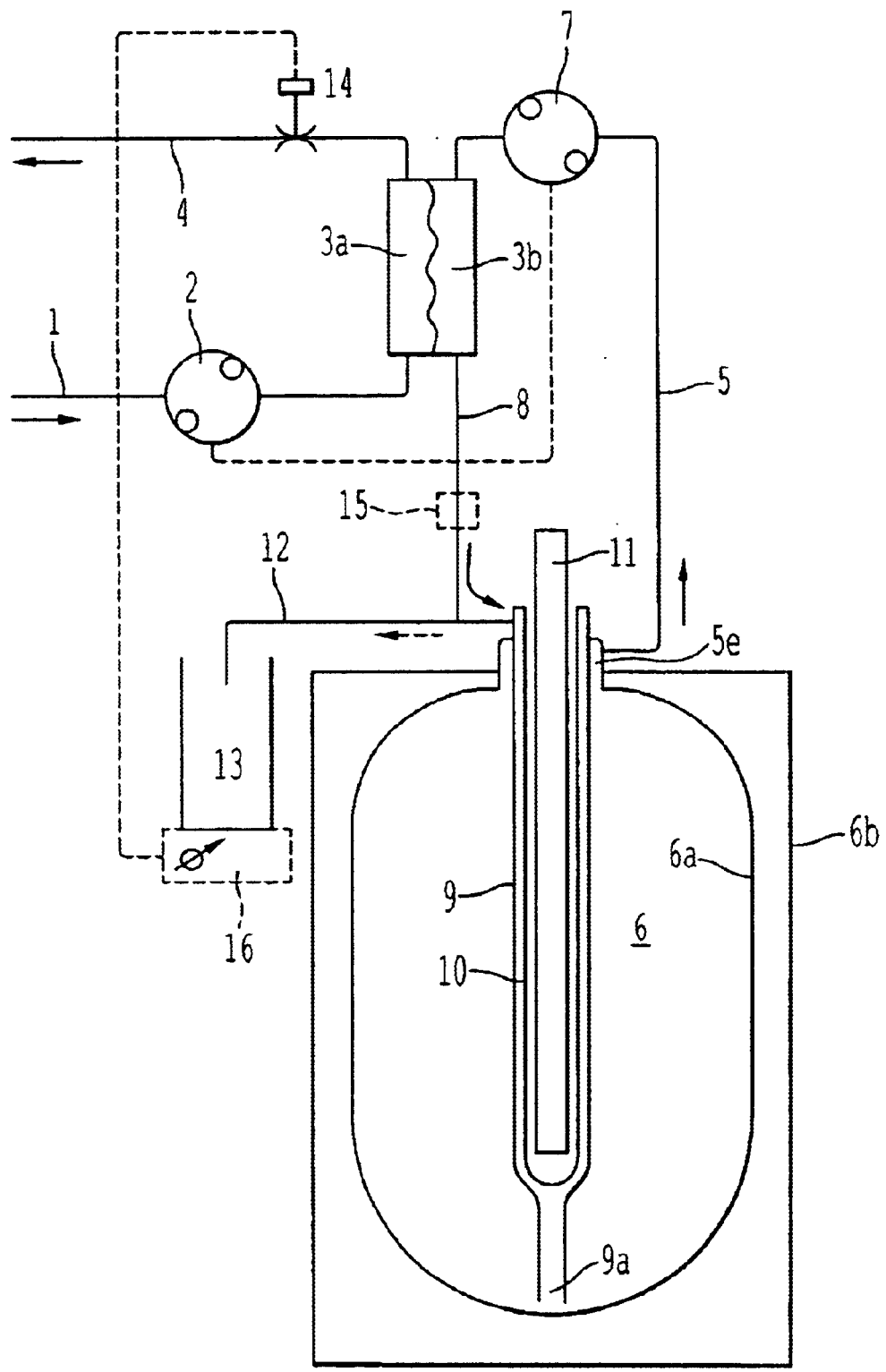
FIG. 1: schematic of an apparatus according to the present invention.

The amino acid concentrations occurring in the plasma of a healthy person are set forth in Table 2:

TABLE 2

| AA | Physiological concentration μmol/l | AA | Physiological concentration μmol/l | AA | Physiological concentration μmol/l |
|---|---|---|---|---|---|
| Gln | 401.8–663.9 | Thr | 103.2–169.1 | Glu | 39.5–88.9 |
| Ala | 339.7–555.2 | Ser | 84.9–138.5 | Phe | 49.1–79.0 |
| Pro | 178.1–355.5 | Arg | 70.1–130.9 | Cys | 50.9–70.0 |
| Val | 206.9–320.8 | His | 76.9–111.8 | Asn | 23.5–61.4 |
| Gly | 175.8–303.9 | Ile | 50.1–99.9 | Trp | 18.4–58.2 |
| Lys | 136.0–231.9 | Tyr | 50.4–91.4 | Cit | 19.3–42.1 |
| Leu | 95.8–180.1 | Orn | 52.2–85.8 | Met | 16.6–33.4 |
| Abu | 10.4–31.8 | Asp | 13.0–22.1 | | |

Heretofore an amino acid mixture for hemodialysis within the composition described above has not been used. The amino acid mixtures used for dialysis to date have never contained all amino acids cited hereinabove, or were originally designed for parenteral nutrition. Such solutions did not and still do not contain all amino acids listed in Table 1. Moreover, the concentration in those solutions is not adapted to the physiological plasma concentration, and so special imbalances not only are not compensated for but in some cases are further exacerbated, to the extent that pathological conditions as serious as hepatogenic encephalopathic coma can develop during continued dialysis.

Another aspect of the invention is the use of the amino acid composition for the preparation of a solution suitable for hemodialysis. In order to adjust the dialyzer fluid to the physiological concentrations listed in Table 2, preferably 0.43 to 0.37 g of the amino acid composition is added per liter of dialyzer solution.

As will be readily appreciated by those skilled in the art, the dialyzer fluid of the present invention may contain the inventive amino acid composition in a fluid medium that is suitable for use in dialysis treatments. The fluid medium may be any which are routinely used in dialysis. For a description of hemodialysis, see *Kirk-Othmer Encyclopedia of Chemical Technology,* Fourth Edition, Volume 8, pp. 64–74, incorporated herein by reference. The fluid medium is preferably an aqueous solution. The aqueous solution may contain appropriate buffers, electrolytes and/or nutrients.

Thus a system has been developed which permits the amino acid composition of the dialyzate to be equivalent to that of the plasma not only in the micromolar respect but also in percentage. This composition and concentration corresponds to the reference ranges of the individual amino acids measured in healthy blood donors (Table 2).

Another aspect of the invention is a hemodialysis method characterized by the use of the amino acid composition according to the invention or the dialyzer fluid according to the invention.

The suitability of the amino acid composition according to the invention as regards prevention of amino acid losses and correction of amino acid imbalances was proved in a 4-week open comparative study with 12 dialysis sessions on 10 patients with chronic kidney diseases of many years standing.

The dialyses were performed with the Genius dialysis system of Teerstegen and Endert (German Patent DE 3115665, incorporated herein by reference), which has a volumetric capacity of 75 liters of inlet solution.

The amino acid composition used had the following absolute or relative composition:

TABLE 3

| AA  | g/batch | rel.   | AA  | g/batch | rel.   |
|-----|---------|--------|-----|---------|--------|
| Gln | 5.8     | 19.02% | Tyr | 0.9     | 2.95%  |
| Ala | 2.9     | 9.51%  | Orn | 0.9     | 2.95%  |
| Pro | 2.3     | 7.54%  | Glu | 0.7     | 2.30%  |
| Val | 2.3     | 7.54%  | Phe | 0.8     | 2.62%  |
| Gly | 1.4     | 4.59%  | Cys | 1.1     | 3.61%  |
| Lys | 2.5     | 8.20%  | Asn | 0.5     | 1.64%  |
| Leu | 1.4     | 4.59%  | Trp | 0.6     | 1.97%  |
| Thr | 1.2     | 3.93%  | Cit | 0.4     | 1.31%  |
| Ser | 0.9     | 2.95%  | Met | 0.3     | 0.98%  |
| Arg | 1.6     | 5.25%  | Abu | 0.0     | 0.00%  |
| His | 1.1     | 3.61%  | Asp | 0.2     | 0.66%  |
| Ile | 0.7     | 2.30%  |     |         |        |

In each case, 30.5 g of this amino acid mixture was dissolved in 75 liters of dialyzer solution.

Dialysis Without Amino Acids

As the study on the patients showed, approximately 8 g of amino acids on average was removed from the body in the dialyzate during each dialysis session. This quantity represents approximately one third of the patient's minimum daily requirement of amino acids.

Dialysis With Physiological Amino Acid Composition

The same study was repeated on the same patients, using the amino acid composition according to the invention. The results show persuasively and clearly that, when the physiological pattern in the inlet dialyzate was applied by increasing the gradient, in the first place amino acids in the physiological concentration range are not lost and, in the second place, the pathological imbalance existing in the plasma, when offered a physiological pattern externally, causes the patient's plasma pattern to adjust to physiological conditions to an extent that under natural conditions would need relatively long-term treatment after years of commercial dialysis therapy and kidney failure with more or less pronounced imbalance. In what is now a relatively short observation period of 4 weeks, trends toward adaptation and elimination of the imbalances are already evident, suggesting for this dialysis form that, not only are amino acids not lost but, by virtue of compensation for the imbalance, a net balance of approximately 1 g in the direction of amino acid incorporation is achieved.

Figure 2:
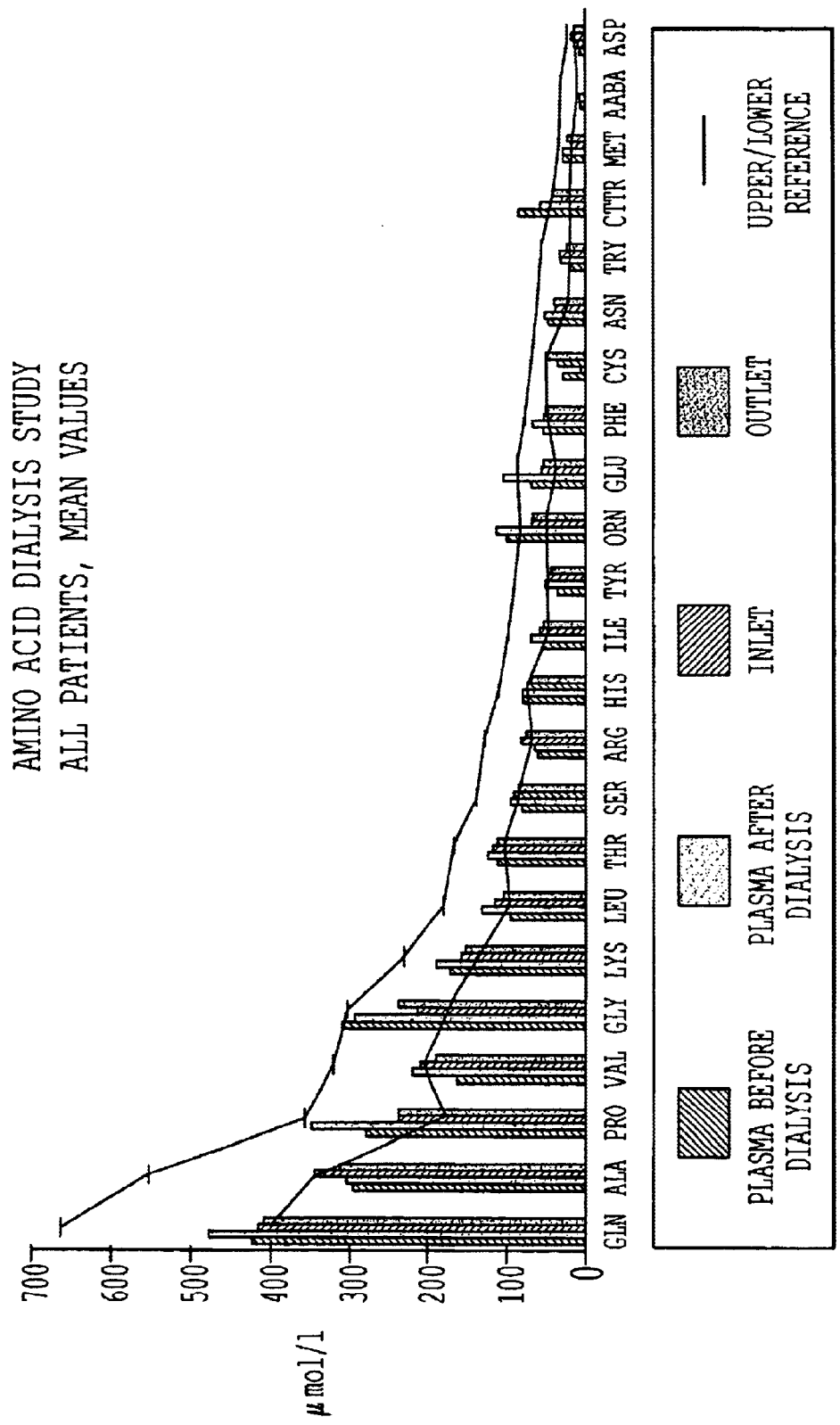
FIG. 2: results of dialysis according to the present invention.
Figure 3:
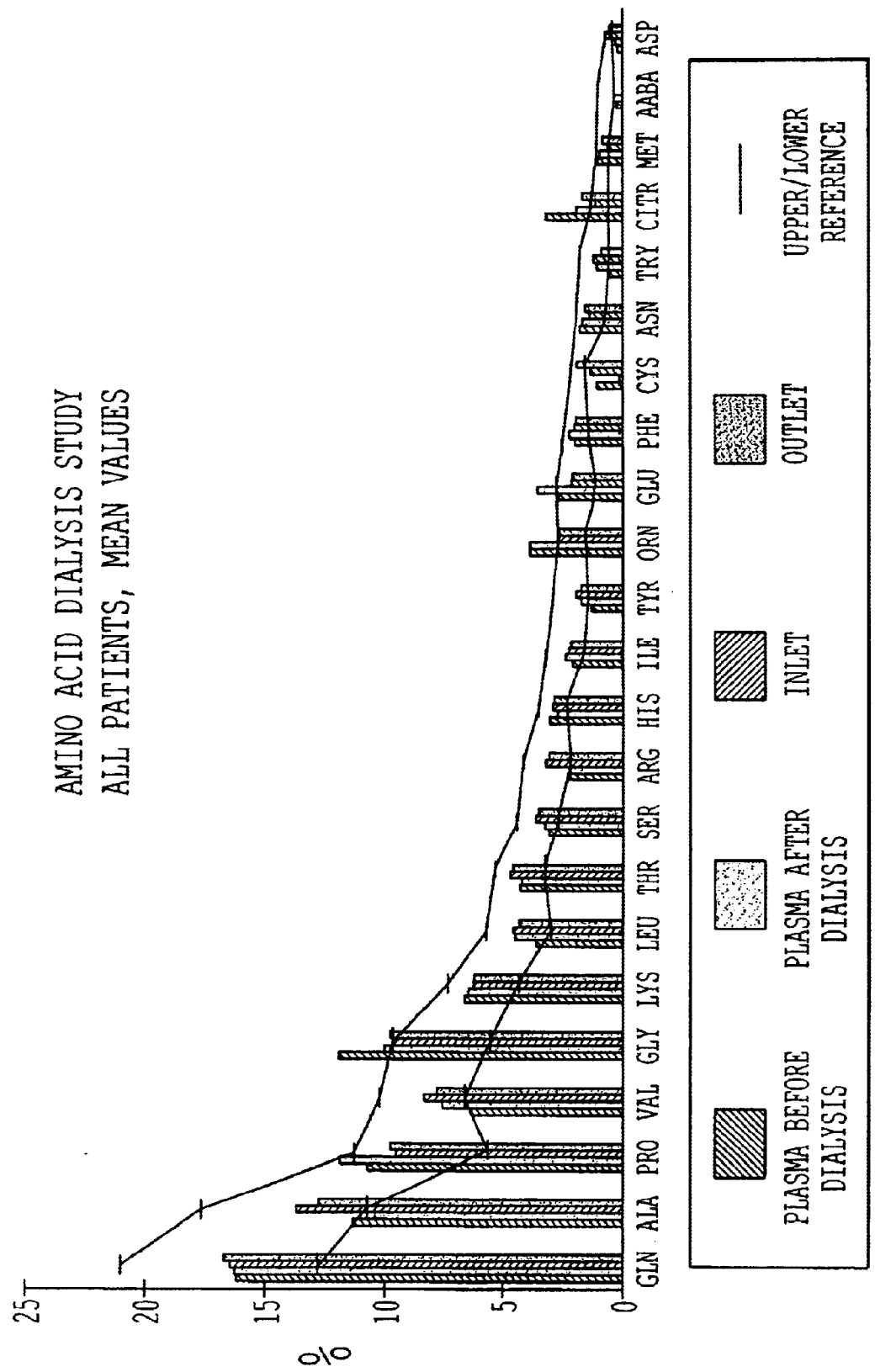
FIG. 3: results of dialysis according to the present invention.

As a result, it can be stated that:

The amino acid analyses of the inlet solution and spent dialysis solution (outlet) show in this study a balance that is negative. In other words, the amino acid concentration in the spent dialysis solution was slightly lower than in the fresh dialysis solution. These changes are brought about by the considerable imbalances in which, as desired, the pathological amino acid concentrations develop, relative to the external physiological composition of the dialyzate solution, a gradient which corrects the pathological changes in the direction of physiological conditions. This effect is evident even in the absolute (micromolar) (FIG. 2) and relative (per cent) (FIG. 3) amino acid distributions, where the most important observation is that the essential amino acids of the branched-chain series (valine, leucine, isoleucine), which in all dialysis patients have concentrations under the physiological reference range, are moving toward the physiological reference range, even after only a few dialysis sessions. Likewise, the amino acids with concentrations pathologically above the reference range, especially glycine, are moving toward the physiological reference range.

By virtue of this amino acid concentration difference between fresh and spent dialyzate, as well as from the change in the amino acid patterns toward physiological conditions, it can be proved on the one hand that amino acid losses which would have to be compensated for by nutrient supply do not occur, and on the other hand that the well-being of the patient also experiences an improvement due to this form of closed dialysis combined with compensation with exogenous amino acids.

The measured values (FIG. 2, 3) represent mean values for ten patients, each treated in twelve dialysis sessions, and so the results are based on a considerable number of amino acid analyses and thereby are also very reliable.

Another aspect of the present invention is a hemodialysis apparatus designed in a manner characteristic of and advantageous for the invention. In particular, the unit uses a dialysis solution containing amino acids in a composition according to the invention.

The dialysis unit with a dialyzer described herein is provided with a first flow path for the blood, a second flow path for the dialyzer fluid and a semipermeable membrane separating the two flow paths, as well as with a vessel containing dialyzer fluid, wherein the dialyzer fluid can be withdrawn via a connection and the spent dialyzer fluid can be returned to the same vessel.

Such a hemodialysis unit has already been described in German Patent DE 3115665. The disclosure therein is incorporated by reference in this description.

Poli et al. describe the positive influence of dialysis by means of dialyzer fluids which contained amino acids in such concentration and composition that the concentration gradient developed on both sides of the dialysis membrane is as small as possible, although detrimental amino acid losses from the patient's body normally occur in the apparatus has correspondingly large dimensions. According to that publication (The International Journal of Artificial Organs 1978, Vol. 1, No. 1, pp. 112 ff.), however, a socalled single-pass system such as described in more detail as prior art in German Patent DE 3115665 was used.

Apart from the disadvantages mentioned in DE 3115665, single-pass systems suffer from critical drawbacks as regards preparing the dialysis fluid and maintaining constant composition thereof. Highly complex apparatus and control systems are therefore needed for continuous production of dialyzer fluid with uniform temperature and constant chemical composition. It is probably because of this additional expense that the technique described by Poli et al. has not yet been widely adopted despite the good results.

Another aspect of the present invention is a simple hemodialysis system which does not suffer from the disadvantages of dialysis systems using physiological amino acid solutions as dialyzer fluid. In particular, the system should be easy to manipulate, inexpensive to operate and robust in application.

By the fact that a hemodialysis unit is equipped with a dialyzer containing a first flow path for the blood, a second flow path for the dialyzer fluid and a semipermeable membrane separating the two flow paths, as well as a vessel for the dialyzer fluid with a connection for withdrawal of dialyzer fluid to be supplied by the dialyzer and with a connection for return to the vessel of the dialyzer fluid arriving from the dialyzer, vessel (6) being sufficiently thermally insulated from the ambient air that there is no need for a heating means to control the temperature of the dialyzer fluid and to keep it constant throughout the duration of the dialysis treatment, and by the fact that connection (5a) for withdrawal of the dialyzer fluid discharges at the upper region of vessel (6) while connection (9a) for return of the dialyzer fluid discharges in the lower region of vessel (6), vessel (6) containing for the upcoming hemodialysis a dialyzer solution of amino acids in dissolved form, the amino acids being present in the composition according to the invention, there is achieved an apparatus which does not suffer from the disadvantages, recognized from known devices, of difficult control of the concentrations of individual substances in the dialyzer fluid and also of the associated expensive measurement and control instrumentation. By virtue of the possibility of the absence of these items of instrumentation, the apparatus is extremely robust and is therefore also suitable for care of dialysis patients outside the outpatient environment.

In one preferred embodiment of the invention, vessel (6) can have double walls and the space between inner vessel (6a) and surrounding additional jacket (6b) can be sealed from the ambient air. It is further advantageous for inner vessel (6a) and jacket (6b) to be made of transparent materials having low thermal conductivity compared with metals. In addition, a radiant heating element can be disposed in the hemodialysis unit, preferably under inner vessel (6a). In this way, it is ensured that the temperature of the dialyzer solution remains constant even during prolonged dialysis sessions.

In a further embodiment, vessel (6) of the hemodialysis unit according to the invention is provided with a means for housing a UV irradiation source (11). In this way easy and efficient disinfection of the dialyzer fluid is possible.

In a preferred embodiment, connection (8) for return of the dialyzer fluid discharges at the upper part of vessel (6) into a tube (9), which is disposed in the interior of the vessel and the end of which is open close to the vessel bottom, Tube (9) is axially disposed, and at its bottom end is provided with a closed inner tube (10) for housing UV irradiation source (11).

In a particularly preferred embodiment, vessel (6) is in communication via an overflow (12) with a measuring instrument (13) for recording any excess fluid volume produced. Furthermore, according to the invention, a flow resistance (14) for adjustment of the ultrafiltration speed can be provided in return line (4) of the first flow path of the dialyzer. In addition, a device for generating a positive backpressure can be provided in the second flow path of the dialyzer.

In an extremely preferred embodiment, a measurement and control instrument (16) measures the excess fluid volume produced, compares the measured value with a specified value and, on the basis of the result of the comparison, automatically adjusts the flow resistance in the return line of the first flow path or the positive backpressure in the second flow path of the dialyzer such that the deviation between measured value and specified value is minimized.

FIG. 1 shows a schematic diagram of a preferred apparatus.

In the illustrated layout, the blood is pumped through a line 1, conveyed by means of a pump 2 through a first flow path 3a of a dialyzer and returned to the patient via a line 4.

The dialyzer fluid flows in countercurrent thereto in a second flow path 3b of the dialyzer. This fluid is withdrawn from vessel 6 through a line 5 with a connection 5a discharging into the vessel, conveyed by means of a pump 7 through flow path 3b of the dialyzer and returned to vessel 6 via a line 8 and a tube 9 discharging at 9a in the lower region of the vessel. Vessel 6 is thermally insulated, specifically to the effect that the temperature of the dialyzer fluid, which was preheated before being introduced, does not drop by more than about 1° C. per hour (internal temperature about 38° C., external temperature about 21° C.). This is preferably achieved by double-walled construction of the vessel, wherein inner vessel 6a is surrounded by an additional jacket 6b, leaving between inner vessel and jacket a free space which is hermetically sealed from the ambient air. Inner vessel 6a and jacket 6b are preferably made of transparent materials, such as glass for the inner vessel and a transparent polymer for the jacket, so that visual inspection is possible. At the same time, these materials have the advantage that their thermal conductivity is lower than that of metals. An inner vessel of glass is bacteriologically and hygienically superior to other materials, since the surface is pore-free. Furthermore, glass is thermally stable and thus favorable for sterilization, largely resistant to chemicals that may be used, can be thoroughly cleaned, and is rigid, volumetrically stable and physiologically safe.

As already mentioned, line 5 discharges at the withdrawal point of the dialyzer fluid at 5a in the upper region of the vessel. Return line 8 discharges into tube 9, which is disposed centrally in the vessel. Thus the spent dialyzer fluid is delivered through open end 9a of tube 9 into the fluid-filled vessel interior in the vicinity of the vessel bottom.

During operation of the hemodialysis unit, mixing between fresh dialyzer fluid and spent dialyzer fluid is avoided; furthermore, the boundary between the clear fresh dialyzer fluid and the dialyzer fluid dyed with ballast materials is readily discernible during operation. In a further embodiment, the vessel is also designed to house an ultraviolet irradiation source. In the illustrated practical example, a closed inner tube 10, into which rod-shaped UV irradiation source 11 is inserted, is provided for this purpose at the bottom end of tube 9, concentrically therewith. Tubes 9 and 10 should be made of material of adequate UV transparency, such as quartz glass.

The excess fluid volume produced by ultrafiltration can be diverted through an overflow from the loop of dialyzer fluid and collected in a measuring vessel 13, wherein the outflow rate can be adjusted by a variable flow resistance on the discharge side of the first flow path of the dialyzer. For this purpose an overflow line 12 leading to a measuring cylinder 13 is connected to the system filled with dialyzer fluid at in principle an arbitrary point, but preferably on the discharge side of the second flow path of the dialyzer. Moreover, a flow restrictor 14 in the form, for example, of a tube clamp, is disposed as a flow resistance on blood return line 4.

Flow restrictor 14 can be used to vary the pressure on the blood side of the dialysis membrane and thus the pressure difference, which is the determining factor for ultrafiltration, between the two sides of the membrane. This flow restrictor is adjusted in such a way, while observing the outflow at the end of overflow 12, that the desired ultrafiltration volume per unit time is obtained. In addition, the total volume of ultrafiltrate collected can be read in the scale of measuring cylinder 13.

The described adjustment method is also characterized by extremely simple apparatus design. Furthermore, it has the advantage, compared to the method described in German Accepted Application DE-AS 2259787, for example, that the pressure in the vessel remains constant, and so the rigidity of the vessel and of the lines connected thereto does not have to meet particularly strict requirements, and even any air volume that may become trapped in the upper part of the vessel does not impair measurement accuracy. In contrast, these problems have a considerable influence in the system illustrated in DE-AS 2259787, because therein the pressure differences caused during adjustment of the ultrafiltration speed can lead to corresponding volume fluctuations. Moreover, additional errors can occur if air is sucked through existing leaks into the vessel because, for example, of the subatmospheric pressure prevailing in the vessel.

In dialyzers with very high membrane permeability, even a low transmembrane pressure is already sufficient to cause considerable ultrafiltration. Thus the situation can occasionally develop in which the pressure prevailing in the blood loop already causes an ultrafiltration speed higher than desired even if flow restrictor 14 is fully open. This can be compensated, however, by a positive backpressure in the dialyzer-fluid loop, for example by interposing a second flow resistance, preferably in the form of a pressure-maintaining valve 15, in return line 8 or in overflow line 12.

The possibility exists in principle of performing the adjustment of the flow restrictor (and if applicable of pressure-maintaining valve 15) by an automatic control system. For this purpose the fluid volume collected in the measuring cylinder or the time change thereof is compared in a measurement and control instrument 16 with an adjustable specified value, and the setting of the flow restrictor is adjusted so as to bring about agreement between actual and specified values.

Furthermore, an infrared heating element can also be provided, preferably disposed under inner vessel 6a. By means of this infrared heating element, the water contained in the inner vessel can be heated for sterilization purposes. The radiation passes through the glass and is then absorbed in the fluid, so that the fluid is heated to boiling point. When the interior space of the inner vessel is sealed against the outside atmosphere, a temperature of about 110° C., as is favorable for sterilization purposes, can be reached at slightly elevated internal pressure.

The hemodialysis apparatus according to the invention is made in simple and thus no less advantageous form by the expedient that, in vessel (6) of an apparatus such as just described, there is mixed a suitable amino acid mixture with a commercially available dialyzer solution not containing amino acids or vice versa, depending on which sequence seems more advantageous from the viewpoint of possible mutual precipitation of constituents. Once a complete solution with stabilized temperature has been formed, the unit according to the invention is ready for dialysis.

By means of the apparatus according to the invention, the amino acid concentration gradient between the dialyzer solution and plasma can be compensated in extremely simple manner with the advantages discussed hereinabove.

Obviously, numerous modifications and variations of the present invention are possible in light of the above teachings. It is therefore to be understood that within the scope of the appended claims, the invention may be practiced otherwise than as specifically described herein.

What is claimed is:

1. An amino acid composition suitable for hemodialysis, comprising amino acids in the following proportions, based on the total weight of the amino acids:

|  | wt % Lower Limit | wt % Upper Limit |
| --- | --- | --- |
| Gln | 15.2 | 22.8 |
| Ala | 7.6 | 11.4 |
| Pro | 6.0 | 9.0 |
| Val | 6.0 | 9.0 |
| Gly | 3.7 | 5.5 |
| Lys | 6.6 | 9.8 |
| Leu | 3.7 | 5.5 |
| Thr | 3.1 | 4.7 |
| Ser | 2.4 | 3.5 |
| Arg | 4.2 | 6.3 |
| His | 2.9 | 4.3 |
| Ile | 1.8 | 2.8 |
| Tyr | 2.4 | 3.5 |
| Orn | 2.4 | 3.5 |
| Glu | 1.8 | 2.8 |
| Phe | 2.1 | 3.1 |
| Cys | 2.9 | 4.3 |
| Asn | 1.3 | 2.0 |
| Trp | 1.6 | 2.4 |
| Cit | 1.0 | 1.6 |
| Met | 0.8 | 1.2 |
| Abu | 0.0 | 0.5 |
| Asp | 0.5 | 0.8. |

2. A dialyzer fluid suitable for hemodialysis, comprising the amino acid composition of claim 1.

3. The dialyzer fluid of claim 2, which is in the form of an aqueous solution.

4. The dialyzer fluid of claim 2, comprising amino acids at the following concentrations:

| Amino Acid | Concentration ($\mu$mol/l) | Amino Acid | Concentration ($\mu$mol/l) | Amino Acid | Concentration ($\mu$mol/l) |
| --- | --- | --- | --- | --- | --- |
| Gln | 401.8–663.9 | Thr | 103.2–169.1 | Glu | 39.5–88.9 |
| Ala | 339.7–555.2 | Ser | 84.9–138.5 | Phe | 49.1–79.0 |
| Pro | 178.1–355.5 | Arg | 70.1–130.9 | Cys | 50.9–70.0 |
| Val | 206.9–320.8 | His | 76.9–111.8 | Asn | 23.5–61.4 |
| Gly | 175.8–303.9 | Ile | 50.1–99.9 | Trp | 18.4–58.2 |
| Lys | 136.0–231.9 | Tyr | 50.4–91.4 | Cit | 19.3–42.1 |
| Leu | 95.8–180.1 | Orn | 52.2–85.8 | Met | 16.6–33.4 |
| Abu | 10.4–31.8 | Asp | 13.0–22.1 | | |

5. A method of preparing the dialyzer fluid of claim 2, comprising incorporating the amino acids into a fluid medium.

6. A method of hemodialysis, comprising dialyzing a patient in need thereof with the amino acid composition of claim 1.

7. A method of hemodialysis, comprising dialyzing a patient in need thereof with the dialyzer fluid of claim 2.

8. A method of hemodialysis, comprising dialyzing a patient in need thereof with the dialyzer fluid of claim 4.

9. A dialyzer fluid suitable for hemodialysis, prepared by a process comprising combining the amino acid composition of claim 1 with a dialyzer fluid.

* * * * *